United States Patent
Helton et al.

(10) Patent No.: US 8,623,777 B2
(45) Date of Patent: Jan. 7, 2014

(54) PROCESS FOR REJUVENATING A CATALYST COMPOSITION

(75) Inventors: Terry Eugene Helton, Bethlehem, PA (US); Vijay Nanda, Houston, TX (US); Wei-Ping Tai, Yardley, PA (US); Teresa Ann Jurgens-Kowal, Houston, TX (US); Kathleen Marie Keville, Beaumont, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 314 days.

(21) Appl. No.: 12/738,061

(22) PCT Filed: Oct. 7, 2008

(86) PCT No.: PCT/US2008/079051
§ 371 (c)(1),
(2), (4) Date: Jul. 20, 2010

(87) PCT Pub. No.: WO2009/058522
PCT Pub. Date: May 7, 2009

(65) Prior Publication Data
US 2010/0285949 A1 Nov. 11, 2010

Related U.S. Application Data

(60) Provisional application No. 60/985,056, filed on Nov. 2, 2007.

(51) Int. Cl.
*B01J 38/04* (2006.01)
*B01J 38/10* (2006.01)
*B01J 38/06* (2006.01)
*B01J 38/02* (2006.01)

(52) U.S. Cl.
USPC .................. 502/53; 502/34; 502/55; 502/56

(58) Field of Classification Search
USPC ..................................... 502/20–56
See application file for complete search history.

(56) References Cited

U.S. PATENT DOCUMENTS

| | | | |
|---|---|---|---|
| 3,418,256 A | 12/1968 | Rigney et al. | |
| 3,751,504 A | 8/1973 | Keown et al. | |
| 3,751,506 A | 8/1973 | Burress | |
| 3,755,483 A | 8/1973 | Burress | |
| 4,439,409 A | 3/1984 | Puppe et al. | |
| 4,810,683 A * | 3/1989 | Cohn et al. | 502/37 |
| 4,826,667 A | 5/1989 | Zones et al. | |
| 4,891,458 A | 1/1990 | Innes et al. | |
| 4,908,341 A | 3/1990 | Pruden et al. | |
| 4,954,325 A | 9/1990 | Rubin et al. | |
| 4,992,606 A | 2/1991 | Kushnerick et al. | |
| 5,149,894 A | 9/1992 | Holtermann et al. | |
| 5,166,454 A * | 11/1992 | Harandi et al. | 568/697 |
| 5,236,575 A | 8/1993 | Bennett et al. | |
| 5,250,277 A | 10/1993 | Kresge et al. | |
| 5,258,565 A | 11/1993 | Kresge et al. | |
| 5,362,697 A | 11/1994 | Fung et al. | |
| 5,371,310 A | 12/1994 | Bennett et al. | |
| 5,405,814 A | 4/1995 | Beech, Jr. et al. | |
| 5,453,554 A | 9/1995 | Cheng et al. | |
| 6,077,498 A | 6/2000 | Diaz Cabañas et al. | |
| 6,218,326 B1 * | 4/2001 | Datta et al. | 502/3 |
| 6,231,751 B1 | 5/2001 | Canos et al. | |
| 6,936,744 B1 | 8/2005 | Cheng et al. | |
| 2008/0027256 A1 | 1/2008 | Roth et al. | |
| 2008/0027259 A1 | 1/2008 | Roth et al. | |
| 2008/0027260 A1 | 1/2008 | Lai et al. | |
| 2008/0045768 A1 | 2/2008 | Roth et al. | |
| 2010/0285949 A1 * | 11/2010 | Helton et al. | 502/53 |

FOREIGN PATENT DOCUMENTS

| | | |
|---|---|---|
| EP | 0 293 032 | 11/1988 |
| EP | 0 432 814 | 6/1991 |
| EP | 0 629 549 | 12/1994 |
| JP | 10-175896 | 6/1998 |

(Continued)

OTHER PUBLICATIONS

Periodic Table, Chemical and Engineering News, Feb. 4, 1985, vol. 63, No. 5, p. 27.
"Atlas of Zeolite Framework Types". Eds. W.H. Meier, D.H. Olson and Ch. Baerlocher, Elsevier, Fifth Edition, 2001.

*Primary Examiner* — Jennifer Smith
(74) *Attorney, Agent, or Firm* — Roberts Mlotkowski Safran & Cole, P.C.

(57) ABSTRACT

This disclosure relates to a method for rejuvenating a catalyst, comprising contacting the catalyst with a gaseous feedstock at rejuvenation conditions for at least one hour to form a rejuvenated catalyst and a gaseous product, wherein the catalyst comprises at least 10 wt. % of a molecular sieve, wherein the catalyst prior to the contacting step comprises from 0.001 wt. % to 45 wt. % of hydrocarbons and 0.001 to 10 wt. % nitrogen containing components based on the total weight of the catalyst prior to the contacting step, wherein the molecular sieve comprises at least one of a MCM-22 family molecular sieve, a molecular sieve having a framework type of *BEA, a molecular sieve having a framework type of FAU, and a molecular sieve having a framework type of MOR, wherein the gaseous feedstock comprises at least one of $N_2$, $H_2$, alkane, He, Ar, CO, and $CO_2$, wherein the gaseous product has at least a portion of the gaseous feedstock and at least a portion of the hydrocarbons of the catalyst and at least a portion of the nitrogen containing components of the catalyst, wherein the rejuvenation conditions comprise a temperature in the range from about 400 to 600° C., a pressure in the range from about 101.3 kPa-a to 10130 kPa-a, a space hourly velocity in the range of from 0.05 to 10 $hr^{-1}$.

13 Claims, No Drawings

(56) References Cited

FOREIGN PATENT DOCUMENTS

| WO | WO 94/20213 | 9/1994 |
| WO | WO 97/17290 | 5/1997 |
| WO | WO 01/83408 | 11/2001 |
| WO | WO 2005/118476 | 12/2005 |
| WO | WO 2006/128649 | 12/2006 |

* cited by examiner

US 8,623,777 B2

PROCESS FOR REJUVENATING A CATALYST COMPOSITION

CROSS-REFERENCE TO RELATED APPLICATIONS

This application is a National Stage Application of International Application No. PCT/US2008/079051 filed Oct. 7, 2008, which claims priority from U.S. Provisional Patent Application No. 60/985,056 filed Nov. 2, 2007, both of which are incorporated herein by reference.

FIELD OF THIS INVENTION

This disclosure relates to a catalyst rejuvenation process.

BACKGROUND OF THIS INVENTION

Molecular sieve materials, both natural and synthetic, have catalytic properties for various types of hydrocarbon conversion. Certain molecular sieves (e.g., zeolites, AlPOs, and/or mesoporous materials) are ordered, porous crystalline materials having a definite crystalline structure. Within the crystalline molecular sieve material there are a large number of cavities which may be interconnected by a number of channels or pores. These cavities and pores are uniform in size within a specific molecular sieve material. Since the dimensions of these pores are such as to accept for adsorption molecules of certain dimensions while rejecting those of larger dimensions, these materials have come to be known as "molecular sieves" and are utilized in a variety of industrial processes.

Such molecular sieves, both natural and synthetic, include a wide variety of positive ion-containing crystalline oxides of tetravalent element. These oxides of tetravalent element can be described as a rigid three-dimensional framework of $YO_4$ and a trivalent element oxide, such as a Group 13 element oxide (e.g., $AlO_4$) (as defined in the Periodic Table, Chemical and Engineering News, 63(5), 27 (1985)). The tetrahedra are cross-linked by the sharing of oxygen atoms whereby the ratio of the total trivalent element (e.g., aluminum) and tetravalent atoms to oxygen atoms is 1:2. The electrovalence of the tetrahedra containing the trivalent element (e.g., aluminum) is balanced by the inclusion in the crystal of a cation, for example a proton, an alkali metal or an alkaline earth metal cation. This can be expressed as the ratio of the trivalent element (e.g., aluminum) to the number of various cations, such as $H^+$, $Ca^{2+}/2$, $Sr^{2+}/2$, $Na^+$, $K^+$, or $Li^+$, being equal to unity.

Molecular sieves that find application in catalysis include any of the naturally occurring or synthetic crystalline molecular sieves. Examples of these sieves include large pore zeolites, intermediate pore size zeolites, and small pore zeolites. These zeolites and their isotypes are described in "Atlas of Zeolite Framework Types", eds. W. H. Meier, D. H. Olson and Ch. Baerlocher, Elsevier, Fifth Edition, 2001, which is herein incorporated by reference. A large pore zeolite generally has a pore size of at least about 7 Å and includes LTL, VFI, MAZ, FAU, OFF, *BEA, and MOR framework type zeolites (IUPAC Commission of Zeolite Nomenclature). Examples of large pore zeolites include mazzite, offretite, zeolite L, VPI-5, zeolite Y, zeolite X, omega, and Beta. An intermediate pore size zeolite generally has a pore size from about 5 Å to less than about 7 Å and includes, for example, MFI, MEL, EUO, MTT, MFS, AEL, AFO, HEU, FER, MWW, and TON framework type zeolites (IUPAC Commission of Zeolite Nomenclature). Examples of intermediate pore size zeolites include ZSM-5, ZSM-11, ZSM-22, "MCM-22 family material", silicalite 1, and silicalite 2. A small pore size zeolite has a pore size from about 3 Å to less than about 5.0 Å and includes, for example, CHA, ERI, KFI, LEV, SOD, and LTA framework type zeolites (IUPAC Commission of Zeolite Nomenclature). Examples of small pore zeolites include ZK-4, ZSM-2, SAPO-34, SAPO-35, ZK-14, SAPO-42, ZK-21, ZK-22, ZK-5, ZK-20, zeolite A, chabazite, zeolite T, gmelinite, ALPO-17, and clinoptilolite.

The term "MCM-22 family material" (or "material of the MCM-22 family" or "molecular sieve of the MCM-22 family"), as used herein, includes one or more of:

(i) molecular sieves made from a common first degree crystalline building block unit cell, which unit cell has the MWW framework topology. (A unit cell is a spatial arrangement of atoms which if tiled in three-dimensional space describes the crystal structure. Such crystal structures are discussed in the "Atlas of Zeolite Framework Types", Fifth edition, 2001, the entire content of which is incorporated as reference);

(ii) molecular sieves made from a common second degree building block, being a 2-dimensional tiling of such MWW framework topology unit cells, forming a monolayer of one unit cell thickness, preferably one c-unit cell thickness;

(iii) molecular sieves made from common second degree building blocks, being layers of one or more than one unit cell thickness, wherein the layer of more than one unit cell thickness is made from stacking, packing, or binding at least two monolayers of one unit cell thickness. The stacking of such second degree building blocks can be in a regular fashion, an irregular fashion, a random fashion, or any combination thereof; and (iv) molecular sieves made by any regular or random 2-dimensional or 3-dimensional combination of unit cells having the MWW framework topology.

The MCM-22 family materials are characterized by having an X-ray diffraction pattern including d-spacing maxima at 12.4±0.25, 3.57±0.07 and 3.42±0.07 Angstroms (either calcined or as-synthesized). The MCM-22 family materials may also be characterized by having an X-ray diffraction pattern including d-spacing maxima at 12.4±0.25, 6.9±0.15, 3.57±0.07 and 3.42±0.07 Angstroms (either calcined or as-synthesized). The X-ray diffraction data used to characterize the molecular sieve are obtained by standard techniques using the K-alpha doublet of copper as the incident radiation and a diffractometer equipped with a scintillation counter and associated computer as the collection system. Materials belong to the MCM-22 family include MCM-22 (described in U.S. Pat. No. 4,954,325 and U.S. patent application Ser. No. 11/823, 722), PSH-3 (described in U.S. Pat. No. 4,439,409), SSZ-25 (described in U.S. Pat. No. 4,826,667), ERB-1 (described in European Patent No. 0293032), ITQ-1 (described in U.S. Pat. No. 6,077,498), ITQ-2 (described in International Patent Publication No. WO97/17290), ITQ-30 (described in International Patent Publication No. WO2005118476), MCM-36 (described in U.S. Pat. No. 5,250,277), MCM-49 (described in U.S. Pat. No. 5,236,575), UZM-8 (described in U.S. Pat. No. 6,756,030), MCM-56 (described in U.S. Pat. No. 5,362, 697), EMM-10-P (described in U.S. patent application Ser. No. 11/823,129), and EMM-10 (described in U.S. patent application Ser. Nos. 11/824,742 and 11/827,953). The entire contents of the patents are incorporated herein by reference.

It is to be appreciated the MCM-22 family molecular sieves described above are distinguished from conventional large pore zeolite alkylation catalysts, such as mordenite, in that the MCM-22 materials have 12-ring surface pockets which do not communicate with the 10-ring internal pore system of the molecular sieve.

The zeolitic materials designated by the IZA-SC as being of the MWW topology are multi-layered materials which have two pore systems arising from the presence of both 10 and 12 membered rings. The Atlas of Zeolite Framework Types classes five differently named materials as having this same topology: MCM-22, ERB-1, ITQ-1, PSH-3, and SSZ-25.

The MCM-22 family molecular sieves have been found to be useful in a variety of hydrocarbon conversion processes. Examples of MCM-22 family molecular sieve are MCM-22, MCM-49, MCM-56, ITQ-1, PSH-3, SSZ-25, and ERB-1. Such molecular sieves are useful for alkylation of aromatic compounds. For example, U.S. Pat. No. 6,936,744 discloses a process for producing a monoalkylated aromatic compound, particularly cumene, comprising the step of contacting a polyalkylated aromatic compound with an alkylatable aromatic compound under at least partial liquid phase conditions and in the presence of a transalkylation catalyst to produce the monoalkylated aromatic compound, wherein the transalkylation catalyst comprises a mixture of at least two different crystalline molecular sieves, wherein each of said molecular sieves is selected from zeolite beta, zeolite Y, mordenite and a material having an X-ray diffraction pattern including d-spacing maxima at 12.4±0.25, 6.9±0.15, 3.57±0.07 and 3.42±0.07 Angstrom (Å).

The MCM-22 family molecular sieves including MCM-22, MCM-49, and MCM-56 have various applications in hydrocarbon conversion processes. Unfortunately, industrial applications of zeolite catalysts have been hindered due to some major disadvantages associated with the current synthesis techniques that make large scale production of these catalysts complicated and therefore expensive. At present, crystalline zeolite catalysts are synthesized mainly by conventional liquid-phase hydrothermal treatment, including in-situ crystallization and seeding method, and the liquid phase transport method.

Ethylbenzene is a key raw material in the production of styrene and is produced by the reaction of ethylene and benzene in the presence of an acid catalyst. Old ethylbenzene production plants, typically built before 1980, used $AlCl_3$ or $BF_3$ as the acidic catalyst. Newer plants have in general been switching to zeolite-based acidic catalysts.

Traditionally, ethylbenzene has been produced in vapor-phase reactor systems, in which the ethylation reaction of benzene with ethylene is carried out at a temperature of about 380-420° C. and a pressure of 9-15 $kg/cm^2$-g in multiple fixed beds of zeolite catalyst. Ethylene exothermally reacts with benzene to form ethylbenzene, although undesirable chain and side reactions also occur. About 15% of the ethylbenzene formed further reacts with ethylene to form di-ethylbenzene isomers (DEB), tri-ethylbenzene isomers (TEB) and heavier aromatic products. All these chain reaction products are commonly referred as polyethylated benzenes (PEBs). In addition to the ethylation reactions, the formation of xylene isomers as trace products occurs by side reactions. This xylene formation in vapor phase processes may yield an ethylbenzene product with about 0.05-0.20 wt. % of xylenes. The xylenes show up as an impurity in the subsequent styrene product, and are generally considered undesirable.

In order to minimize the formation of PEBs, a stoichiometric excess of benzene, about 400-2000% per pass, is applied, depending on process optimization. The effluent from the ethylation reactor contains about 70-85 wt. % of unreacted benzene, about 12-20 wt. % of ethylbenzene product and about 3-4 wt. % of PEBs. To avoid a yield loss, the PEBs are converted back to ethylbenzene by transalkylation with additional benzene, normally in a separate transalkylation reactor.

By way of example, vapor phase ethylation of benzene over the crystalline aluminosilicate zeolite ZSM-5 is disclosed in U.S. Pat. No. 3,751,504 (Keown et al.), U.S. Pat. No. 3,751,506 (Burress), and U.S. Pat. No. 3,755,483 (Burress).

In recent years the trend in industry has been to shift away from vapor phase reactors to liquid phase reactors. Liquid phase reactors operate at a temperature of about 180-270° C., which is under the critical temperature of benzene (about 290° C.). One advantage of the liquid phase reactor is the very low formation of xylenes and other undesirable byproducts. The rate of the ethylation reaction is normally lower compared with the vapor phase, but the lower design temperature of the liquid phase reaction usually economically compensates for the negatives associated with the higher catalyst volume. Thus, due to the kinetics of the lower ethylation temperatures, resulting from the liquid phase catalyst, the rate of the chain reactions forming PEBs is considerably lower; namely, about 5-8% of the ethylbenzene is converted to PEBs in liquid phase reactions versus the 15-20% converted in vapor phase reactions. Hence the stoichiometric excess of benzene in liquid phase systems is typically 150-400%, compared with 400-2000% in vapor phase.

Liquid phase ethylation of benzene using zeolite beta as the catalyst is disclosed in U.S. Pat. No. 4,891,458 and European Patent Publication Nos. 0432814 and 0629549. More recently it has been disclosed that MCM-22 and its structural analogues have utility in these alkylation/transalkylation reactions, see, for example, U.S. Pat. No. 4,992,606 (MCM-22), U.S. Pat. No. 5,258,565 (MCM-36), U.S. Pat. No. 5,371,310 (MCM-49), U.S. Pat. No. 5,453,554 (MCM-56), U.S. Pat. No. 5,149,894 (SSZ-25); U.S. Pat. No. 6,077,498 (ITQ-1); and U.S. Pat. No. 6,231,751 (ITQ-2).

Although liquid phase ethylbenzene plants offer significant advantages over vapor phase processes, because they necessarily operate at lower temperatures, liquid phase processes tend to be more sensitive to catalyst poisons than their vapor phase counterparts, making them of limited utility with lower grade ethylene and benzene streams without significant feed pretreatment. However, the purification of alkylation feed streams is a costly business and hence there is considerable interest in developing processes that may operate with lower grade feed streams.

After catalyst is brought on stream for a period of time, the catalyst normally will be deactivated due to coking, or depositing of hydrocarbons, especially nitrogen containing components. After deactivation, the catalyst normally needs to be regenerated to remove coke and poisons such as nitrogen and sulfur. Typically the regeneration is performed "in-situ" or "ex-situ" by burning the spent catalyst in air. Some catalyst is sensitive to the amount of moisture in the air. Also water is formed during the combustion process of removing the carbon from the catalyst.

We have found that an inert gas rejuvenation instead of an air regeneration is adequate for removing the carbon, nitrogen, and sulfur compounds of the spent catalyst, especially for spent catalyst in an alkylation process.

SUMMARY OF THIS INVENTION

In some embodiments, this disclosure relates to a method for synthesizing a method for rejuvenating a catalyst, comprising contacting the catalyst with a gaseous feedstock at rejuvenation conditions for at least one hour, preferably from 1 hour to 10 days, more preferably from 12 hours to 5 days, most preferably from 24 hours to 3 days, to form a rejuvenated catalyst and a gaseous product, wherein the catalyst comprises at least 10 wt. %, preferably 50 wt. %, of a molecular sieve, wherein the catalyst prior to the contacting step comprises from 0.001 wt. % to 45 wt. %, preferably 0.1 wt. % to 10 wt. %, of hydrocarbons and 0.001 to 10 wt. %, preferably 0.01 to 5 wt. %, nitrogen containing components based on the total weight of the catalyst prior to the contacting step, wherein the molecular sieve comprises at least one of a MCM-22 family molecular sieve, a molecular sieve having a framework type of *BEA, a molecular sieve having a framework type of FAU, and a molecular sieve having a framework type of MOR, wherein the gaseous feedstock comprises at least one of $N_2$, $H_2$, alkane, He, Ar, CO, and $CO_2$, wherein the gaseous product has at least a portion of the gaseous feedstock and at least a portion of the hydrocarbons of the catalyst and at least a portion of the nitrogen containing components of the catalyst, wherein the rejuvenation conditions comprise a temperature in the range from about 400 to 600° C., preferably from about 500 to 560° C., more preferably from about 530 to 550° C., a pressure in the range from about 101.3 kPa-a to 10130 kPa-a, a space hourly velocity in the range of from 0.05 to 10 normal cubic meter gaseous feedstock per hour per kilogram of catalyst, preferably from about 0.1 to 2.5 normal cubic meter gaseous feedstock per hour per kilogram of catalyst, and more preferably from about 0.5 to 1.5 normal cubic meter gaseous feedstock per hour per kilogram of catalyst.

In some aspects, the rejuvenated catalyst comprises at least 50 wt. % less hydrocarbons and at least 50 wt. % less nitrogen containing components than the catalyst prior to the contacting step.

In other aspects, the gaseous feedstock comprises less than 5 vol. % of nitrogen containing compounds (not including $N_2$). In further aspects, the gaseous feedstock comprises less than 1 wt. % water.

In some embodiments, the molecular sieve is a MCM-22 family molecular sieve. In a preferred embodiment, the molecular sieve comprises at least one MCM-22, MCM-49, MCM-56, zeolite beta, zeolite Y, and zeolite mordenite.

In another preferred embodiment, the gaseous feedstock comprises at least 95 wt. % nitrogen.

In some embodiments, the method of this disclosure further comprises a step of recycling at least a portion of the gaseous product to the contacting step (a). In a preferred embodiment, the method of this disclosure recycles less than 90 wt. %, such as less than 80 wt. % or less than 75 wt. %, of the gaseous product to the contacting step (a).

In some embodiments, the method of this disclosure further comprises a step of separating at least a portion of the hydrocarbons and at least a portion of the nitrogen containing components in the gaseous product. In a preferred embodiment, the separating step is prior to the recycling step.

In some embodiments, the catalyst is a spent catalyst of an ethylbenzene process or a cumene process.

In other embodiments, this disclosure relates to a catalyst composition made by the method of this disclosure.

DETAILED DESCRIPTION OF THIS INVENTION

As used in this specification, the term "framework type" is used in the sense described in the "Atlas of Zeolite Framework Types," 2001.

As used herein, the numbering scheme for the Periodic Table Groups is used as in Chemical and Engineering News, 63(5), 27 (1985).

The term "wppm" as used herein is defined as parts per million by weight.

The term "nitrogen containing components" as used herein mean a compound having at least one nitrogen atom per molecule, such ammonia and pyridine, except nitrogen.

The term "hydrocarbons" on the catalyst as used herein mean hydrocarbon adsorbed (physically or chemically) on the catalyst. The term "hydrocarbons" on the catalyst as used herein also includes coke deposited on the catalyst.

Rejuvenation Catalyst

In some embodiments, this disclosure relates to a method for synthesizing a method for rejuvenating a catalyst, comprising contacting the catalyst with a gaseous feedstock at rejuvenation conditions for at least one hour, preferably from 1 hour to 10 days, more preferably from 12 hours to 5 days, most preferably from 24 hours to 3 days, to form a rejuvenated catalyst and a gaseous product, wherein the catalyst comprises at least 10 wt. %, preferably 50 wt. %, of a molecular sieve, wherein the catalyst prior to the contacting step comprises from 0.001 wt. % to 45 wt. %, preferably 0.1 wt. % to 10 wt. %, of hydrocarbons and 0.001 to 10 wt. %, preferably 0.01 to 5 wt. %, nitrogen containing components based on the total weight of the catalyst prior to the contacting step, wherein the molecular sieve comprises at least one of a MCM-22 family molecular sieve, a molecular sieve having a framework type of *BEA, a molecular sieve having a framework type of FAU, and a molecular sieve having a framework type of MOR, wherein the gaseous feedstock comprises at least one of $N_2$, $H_2$, alkane, He, Ar, CO, and $CO_2$, wherein the gaseous product has at least a portion of the gaseous feedstock and at least a portion of the hydrocarbons of the catalyst and at least a portion of the nitrogen containing components of the catalyst, wherein the rejuvenation conditions comprise a temperature in the range from about 400 to 600° C., preferably from about 500 to 560° C., more preferably from about 530 to 550° C., a pressure in the range from about 101.3 kPa-a to 10130 kPa-a, a space hourly velocity in the range of from 0.05 to 10 normal cubic meter gaseous feedstock per hour per kilogram of catalyst, preferably from about 0.1 to 2.5 $hr^{-1}$, and more preferably from about 0.5 to 1.5 $hr^{-1}$.

The catalyst composition or the catalyst composition rejuvenated by the method of this disclosure is useful as catalyst in a wide range of processes, including separation processes and hydrocarbon conversion processes. Specific examples of hydrocarbon conversion processes which are effectively catalyzed by the crystalline molecular sieve(s) of this disclosure by itself or in combination with one or more other catalytically active substances including other crystalline molecular sieves, include the following:

(i) alkylation of aromatic hydrocarbons, e.g., benzene, with long chain olefins, e.g., $C_{14}$ olefin, with reaction conditions including, individually or in any combination, a temperature of from about 340° C. to about 500° C., a pressure of from about 101 to about 20200 kPa-a (absolute), a weight hourly space velocity of from about 2 $hr^{-1}$ to about 2000 $hr^{-1}$ and an aromatic hydrocarbon/olefin mole ratio of from about 1/1 to about 20/1, to provide long chain alkyl aromatics which can be subsequently sulfonated to provide synthetic detergents;

(ii) alkylation of aromatic hydrocarbons with gaseous olefins to provide short chain alkyl aromatic compounds, e.g., the alkylation of benzene with propylene to provide cumene, with reaction conditions including, individually or in any combination, a temperature of from about 10° C. to about 125° C., a pressure of from about 101 to about 3030 kPa-a, and an aromatic hydrocarbon weight hourly space velocity (WHSV) of from 5 $hr^{-1}$ to about 50 $hr^{-1}$;

(iii) alkylation of reformate containing substantial quantities of benzene and toluene with fuel gas containing $C_5$ olefins to provide, inter alia, mono- and di-alkylates with reaction conditions including, individually or in any combination, a temperature of from about 315° C. to about 455° C., a pressure of from about 3000 to about 6000 kPa-a, a WHSV-olefin of from about 0.4 hr$^{-1}$ to about 0.8 hr$^{-1}$, a WHSV-reformate of from about 1 hr$^{-1}$ to about 2 hr$^{-1}$ and a gas recycle of from about 1.5 to 2.5 vol/vol fuel gas feed;

(iv) alkylation of aromatic hydrocarbons, e.g., benzene, toluene, xylene and naphthalene, with long chain olefins, e.g., $C_{14}$ olefin, to provide alkylated aromatic lube base stocks with reaction conditions including, individually or in any combination, a temperature of from about 160° C. to about 260° C. and a pressure of from about 2600 to 3500 kPa-a;

(v) alkylation of phenols with olefins or equivalent alcohols to provide long chain alkyl phenols with reaction conditions including, individually or in any combination, a temperature of from about 200° C. to about 250° C., a pressure of from about 1500 to 2300 kPa-a and a total WHSV of from about 2 hr$^{-1}$ to about 10 hr$^{-1}$;

(vi) conversion of light paraffins to olefins and aromatics with reaction conditions including, individually or in any combination, a temperature of from about 425° C. to about 760° C. and a pressure of from about 170 to about 15000 kPa-a;

(vii) conversion of light olefins to gasoline, distillate and lube range hydrocarbons with reaction conditions including, individually or in any combination, a temperature of from about 175° C. to about 375° C. and a pressure of from about 800 to about 15000 kPa-a;

(viii) two-stage hydrocracking for upgrading hydrocarbon streams having initial boiling points above about 260° C. to premium distillate and gasoline boiling range products in a first stage using the MCM-22 family molecular sieve of this disclosure in combination with a Groups 8-10 metal as catalyst with effluent therefrom being reaction in a second stage using zeolite Beta, also in combination with a Groups 8-10 metal, as catalyst, the reaction conditions including, individually or in any combination, a temperature of from about 340° C. to about 455° C., a pressure of from about 3000 to about 18000 kPa-a, a hydrogen circulation of from about 176 to about 1760 liter/liter and a liquid hourly space velocity (LHSV) of from about 0.1 to 10 h$^{-1}$;

(ix) a combination hydrocracking/dewaxing process in the presence of the MCM-22 family molecular sieve of this disclosure and a hydrogenation component as catalyst, or a mixture of such catalyst and zeolite Beta, with reaction conditions including, individually or in any combination, a temperature of from about 350° C. to about 400° C., a pressure of from about 10000 to about 11000 kPa-a, an LHSV of from about 0.4 to about 0.6 and a hydrogen circulation of from about 528 to about 880 liter/liter;

(x) reaction of alcohols with olefins to provide mixed ethers, e.g., the reaction of methanol with isobutene and/or isopentene to provide methyl-t-butyl ether (MTBE) and/or t-amyl methyl ether (TAM) with conversion conditions including, individually or in any combination, a temperature of from about 20° C. to about 200° C., a pressure of from 200 to about 20000 kPa-a, a WHSV (gram-olefin per hour gram-zeolite) of from about 0.1 hr$^{-1}$ to about 200 hr$^{-1}$ and an alcohol to olefin molar feed ratio of from about 0.1/1 to about 5/1;

(xi) toluene disproportionation with $C_9$+ aromatics as co-feed with reaction conditions including, individually or in any combination, a temperature of from about 315° C. to about 595° C., a pressure of from about 101 to about 7200 kPa-a, a hydrogen/hydrocarbon mole ratio of from about 0 (no added hydrogen) to about 10 and a WHSV of from about 0.1 hr$^{-1}$ to about 30 hr$^{-1}$;

(xii) preparation of the pharmaceutically-active compound 2-(4-isobutylphenyl) propionic acid, i.e. ibuprofen, by reacting isobutyl benzene with propylene oxide to provide the intermediate 2-(4-isobutylphenyl) propanol followed by oxidation of the alcohol to the corresponding carboxylic acid;

(xiii) use as an acid-binding agent in the reaction of amines with heterocyclic fiber-reactive components in preparation of dyes to prepare practically salt-free reactive dye-containing solution, as in German Patent No. DE 3,625, 693, incorporated entirely herein by reference;

(xiv) as the absorbent for separating 2,6-toluene diisocyanate (2,6-TDI) from isomers if TDI as in U.S. Pat. No. 4,721,807, incorporated entirely herein by reference, whereby a feed mixture comprising 2,6-TDI and 2,4-TDI is contacted with the present MCM-22 family molecular sieve which has been cation-exchanged with K ions to absorb the 2,6-TDI, followed by recovering the 2,6-TDI by desorption with desorbent material comprising toluene;

(xv) as the absorbent for separating 2,4-TDI from its isomers as in U.S. Pat. No. 4,721,806, incorporated entirely herein by reference, whereby a feed mixture comprising 2,4-TDI and 2,6-TDI is contact with the present MCM-22 family molecular sieve which has been cation-exchanged with Na, Ca Li and/or Mg ions to absorb the 2,4-TDI, followed by recovering the 2,4-TDI by desorption with desorbent material comprising toluene;

(xvi) in a process for decreasing the durene content of a 90-200° C.+ bottoms fraction obtained from the catalytic conversion of methanol to gasoline which comprises contacting the durene-containing bottoms fraction with hydrogen over a catalyst of the present MCM-22 family molecular sieve with a hydrogenation metal, at conditions including, individually or in any combination, a temperature of from about 230° C. to about 425° C. and a pressure of from about 457 to about 22000 kPa-a;

(xvii) in a processes for co-producing phenol and ketones that proceed through benzene alkylation, followed by formation of the alkylbenzene hydroperoxide and cleavage of the alkylbenzene hydroperoxide into phenol and ketone, e.g., benzene and propylene to phenol and acetone, benzene and $C_4$ olefins to phenol and methyl ethyl ketone, such as those described for example in international application PCT/EP2005/008557, which can be followed by conversion of phenol and acetone to bis-phenol-A as described in international application PCT/EP2005/008554, benzene to phenol and cyclohexanone, or benzene and ethylene to phenol and methyl ethyl ketone, as described for example in PCT/EP2005/ 008551;

(xviii) in a process of benzene alkylation reactions where selectivity to the monoalkylbenzene is required, e.g., selectively sec-butylbenzene from benzene and $C_4$ olefin feeds that are rich in linear butenes, as described in international application PCT/EP2005/008557, preferably, this conversion is carried out by co-feeding benzene and the $C_4$ olefin feed with the catalyst of the present invention, at a temperature of about 60° C. to about 260° C., for example of about 100° C. to 200° C., a pressure of 7000 kPa-a or less, and a feed weight hourly space velocity (WHSV) based on $C_4$ alkylating agent of from about 0.1 to 50 $h^{-1}$ and a molar ratio of benzene to $C_4$ alkylating agent from about 1 to about 50; and (xix) in a process for transalkylations, such as, for example, polyalkylbenzene transalkylations.

The Alkylation and/or the Transalkylation Process

The reactants used in the present process include an alkylatable aromatic compound and an alkene alkylating agent.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a heteroatom are also useful provided they do not act as catalyst poisons under the reaction conditions selected.

Substituted aromatic compounds which may be alkylated herein must possess at least one hydrogen atom directly bonded to the aromatic nucleus. The aromatic rings may be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which may be present as substituents on the aromatic compound contain from about 1 to 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, mesitylene, durene, cymenes, butylbenzene, pseudocumene, o-diethylbenzene, m-diethylbenzene, p-diethylbenzene, isoamylbenzene, isohexylbenzene, pentaethylbenzene, pentamethylbenzene; 1,2, 3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalenes; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons may also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene, pentadecytoluene, etc. Very often alkylate is obtained as a high boiling fraction in which the alkyl group attached to the aromatic nucleus varies in size from about $C_6$ to about $C_{12}$.

Reformate or a cut thereof containing substantial quantities of benzene, toluene and/or xylene constitutes a particularly useful feed for the alkylation process of this invention.

The alkylating agent useful in the present process includes an alkene, which can be present as substantially pure alkene feed or as a dilute feed containing at least one alkane and typically at least one alkane having the same number of carbon atoms as the alkene. For example, where the alkene is ethylene, the alkane may be ethane. Typically, the dilute alkene feed comprises at least 20 wt. % of the alkene, such as from about 20 to about 80 wt. %, for example from about 60 to about 80 wt. %, of the alkene. It is recognized that feed sources may undergo purification (for example by distillation) prior to being fed to the present process. One particularly useful feed is the dilute ethylene stream obtained as an off gas from the fluid catalytic cracking unit of a petroleum refinery.

Preferably, the reactants in the present process are benzene and ethylene and the desired reaction product is ethylbenzene.

Vapor Phase Alkylation

The vapor phase alkylation typically the alkylatable aromatic compound includes benzene, the alkene includes ethylene and the alkylaromatic compound includes ethylbenzene, the conditions in the or each alkylation reaction zone of the first alkylation reaction system include a temperature of about 350° C. to about 400° C. and a pressure of about 2000 kPa-a to about 3500 kPa-a.

In one embodiment, the alkylation catalyst employed in the or each alkylation reaction zone of the vapor phase alkylation reaction system comprises at least one medium pore molecular sieve having a Constraint Index of 2-12 (as defined in U.S. Pat. No. 4,016,218). Suitable medium pore molecular sieves include ZSM-5, ZSM-11, ZSM-12, ZSM-22, ZSM-23, ZSM-35, and ZSM-48. ZSM-5 is described in detail in U.S. Pat. Nos. 3,702,886 and Re. 29,948. ZSM-11 is described in detail in U.S. Pat. No. 3,709,979. ZSM-12 is described in U.S. Pat. No. 3,832,449. ZSM-22 is described in U.S. Pat. No. 4,556, 477. ZSM-23 is described in U.S. Pat. No. 4,076,842. ZSM-35 is described in U.S. Pat. No. 4,016,245. ZSM-48 is more particularly described in U.S. Pat. No. 4,234,231.

In a further embodiment, the alkylation catalyst employed in the or each alkylation reaction zone of the vapor phase alkylation reaction system comprises one or more large pore molecular sieves having a Constraint Index less than 2. Suitable large pore molecular sieves include zeolite beta, zeolite Y, Ultrastable Y (USY), Dealuminized Y (DealY), mordenite, ZSM-3, ZSM-4, ZSM-18, and ZSM-20. Zeolite ZSM-14 is described in U.S. Pat. No. 3,923,636. Zeolite ZSM-20 is described in U.S. Pat. No. 3,972,983. Zeolite Beta is described in U.S. Pat. No. 3,308,069, and Re. No. 28,341. Low sodium Ultrastable Y molecular sieve (USY) is described in U.S. Pat. Nos. 3,293,192 and 3,449,070. Dealuminized Y zeolite (Deal Y) may be prepared by the method found in U.S. Pat. No. 3,442,795. Zeolite UHP-Y is described in U.S. Pat. No. 4,401,556. Mordenite is a naturally occurring material but is also available in synthetic forms, such as TEA-mordenite (i.e., synthetic mordenite prepared from a reaction mixture comprising a tetraethylammonium directing agent). TEA-mordenite is disclosed in U.S. Pat. Nos. 3,766, 093 and 3,894,104.

Preferred molecular sieves for the vapor phase alkylation reaction comprise zeolite beta, molecular sieves having a Constraint Index of 2-12, especially ZSM-5, and molecular sieves of the MCM-22 family.

The above molecular sieves may be used as the vapor phase alkylation catalyst without any binder or matrix, i.e., in so-called self-bound form. Alternatively, the molecular sieve may be composited with another material which is resistant to the temperatures and other conditions employed in the alkylation reaction. Such materials include active and inactive materials and synthetic or naturally occurring zeolites as well as inorganic materials such as clays and/or oxides such as alumina, silica, silica-alumina, zirconia, titania, magnesia or mixtures of these and other oxides. The latter may be either naturally occurring or in the form of gelatinous precipitates or gels including mixtures of silica and metal oxides. Clays may also be included with the oxide type binders to modify the mechanical properties of the catalyst or to assist in its manufacture. Use of a material in conjunction with the molecular sieve, i.e., combined therewith or present during its synthesis, which itself is catalytically active may change the conversion and/or selectivity of the catalyst. Inactive materials suitably serve as diluents to control the amount of conversion so that products may be obtained economically and orderly without employing other means for controlling the rate of reaction. These materials may be incorporated into naturally occurring clays, e.g., bentonite and kaolin, to improve the crush strength of the catalyst under commercial operating conditions and function as binders or matrices for the catalyst. The relative proportions of molecular sieve and inorganic oxide matrix vary widely, with the sieve content ranging from about 1 to about 90 percent by weight and more usually, particularly, when the composite is prepared in the form of beads, in the range of about 2 to about 80 weight percent of the composite.

The effluent from the vapor phase alkylation reaction system comprises the desired alkylaromatic compound, together with polyalkylated species, such as di- and triethylbenzene, unreacted alkylatable aromatic compound, any unreacted alkene (overall alkene conversion is expected to be 98-99.99+%) and any unreactive impurities present in the original alkene and aromatic feeds. Examples of typical impurities include N-methylpyrrolidone (NMP) and sulfolane typically present in benzene feedstocks and dimethylformamide (DMF) often present in ethylene feeds. Depending on the nature of these unreactive impurities, they could adversely affect the downstream liquid phase alkylation step and hence part or all of the vapor phase alkylation effluent treated before being fed to liquid phase alkylation system. In one embodiment, the treating step is carried out in a pretreater. The pretreater is designed to remove catalyst poisons from the vapor phase alkylation effluent and typically contains a material, such as clay, activated carbon, alumina and/or a molecular sieve, capable of removing sulfur and nitrogen-containing impurities from the effluent. The pretreater is typically operated at a temperature of about 25° C. to about 200° C.

After passage through the pretreater, the vapor phase alkylation effluent is fed to a product separation system where the unreacted alkylatable aromatic compound is separated from the desired alkylaromatic compound and any polyalkylated species before being fed to the liquid phase alkylation system. In some cases, prior to feeding the vapor phase alkylation effluent to the pretreater, it may be desirable to subject the effluent to an initial fractionation step to remove part of the unreacted alkylatable aromatic compound for recycle to the vapor phase alkylation system and, if necessary to remove water that may have been present in the fresh benzene feed.

Liquid Phase Alkylation

The liquid phase alkylation typically, where the alkylatable aromatic compound includes benzene, the alkene includes ethylene and the alkylaromatic compound includes ethylbenzene, the conditions in the or each liquid phase alkylation reaction zone include a temperature of about 120° C. to about 270° C. and a pressure of about 675 kPa-a to about 8300 kPa-a.

The alkene feedstock employed in the second liquid phase alkylation reaction system can be the same as or different from the alkene feedstock employed in the first vapor phase alkylation reaction system, although the alkene component in each feedstock will generally be the same, such as ethylene. In particular, if the vapor phase alkene feedstock contains nitrogenous impurities, a different feedstock or the same feedstock but treated to remove the nitrogenous impurities will generally be used for the liquid phase reaction. Typically, the vapor phase alkene feedstock can contain up to 0.01 wt. % nitrogen-containing impurities as elemental nitrogen, whereas the liquid phase alkene feedstock should contain less than 0.001 wt. % nitrogen-containing impurities as elemental nitrogen.

For example, treatment of the liquid phase alkene feedstock to remove nitrogenous impurities can be achieved by providing a by-passable reactive guard bed upstream of the second liquid phase alkylation reaction system. The reactive guard bed is also loaded with alkylation catalyst, which may be the same of different from the catalyst used in the or each liquid phase alkylation reaction zone, and is maintained under ambient or up to alkylation conditions. The alkylatable aromatic compound and at least a portion of the alkene feedstock are passed through the reactive guard bed prior to entry into the or the first liquid phase alkylation reaction zone. The reactive guard bed not only serves to effect the desired alkylation reaction but is also used to remove any reactive impurities in the feeds, such as nitrogen compounds, which could otherwise poison the remainder of the liquid phase alkylation catalyst. The catalyst in the guard bed is therefore subject to more frequent regeneration and/or replacement than the remainder of the liquid phase alkylation catalyst and hence the guard bed is normally provided with a by-pass circuit so that the alkylation feedstocks may be fed directly to the liquid phase alkylation reaction system when the guard bed is out of service.

The alkylation catalyst employed in the or each alkylation reaction zone of the liquid phase alkylation reaction system can comprise one or more of any of the molecular sieves discussed above in relation to the vapor phase alkylation system and can be used with or without a binder or matrix. Generally, however, the liquid phase alkylation catalyst is selected from zeolite beta and a molecular sieve of the MCM-22 family.

In addition to the desired alkylaromatic product, the effluent from the liquid phase alkylation step tends to contain significant quantities of unreacted alkylatable aromatic compound and, in some cases, it may be desirable to remove at least part of said unreacted alkylatable aromatic compound and recycle it to the liquid phase alkylation step.

Transalkylation

The effluent from the vapor phase alkylation system or the effluent from the liquid phase alkylation system, will tend to contain polyalkylated aromatic compounds. Thus the or each effluents are passed to the product separation system that not only serves to remove unreacted alkylated aromatic compound, and desired monoalkylated product, but also separates the polyalkylated species. The polyalkylated species are then fed to a transalkylation reactor, which is normally separate from the alkylation reactor, where additional monoalkylated product is produced by reacting the polyalkylated species with additional aromatic compound in the presence of a transalkylation catalyst. Typically, the transalkylation reactor is operated under conditions such that the polyalkylated aromatic compounds and the alkylatable aromatic compound are at least predominantly in the liquid phase.

For example, suitable conditions for carrying out the liquid phase transalkylation of benzene with polyethylbenzenes may include a temperature of from about 150° C. to about 260° C., a pressure of 7000 kPa-a or less, a WHSV based on the weight of the total liquid feed to the reaction zone of from about 0.5 to about 100 $hr^{-1}$ and a mole ratio of benzene to polyethylbenzene of from about 1:1 to about 30:1. Particular conditions for carrying out the liquid phase transalkylation of benzene with polypropylbenzenes may include a temperature of from about 150° C. to about 300° C., a pressure of 5500 kPa-a or less, a WHSV based on the weight of the total liquid feed to the reaction zone of from about 0.1 to about 20.0 $hr^{-1}$ and a mole ratio of benzene to polypropylbenzene of from about 1.0 to about 10.0. Particular conditions for carrying out the liquid phase transalkylation of benzene with polybutylbenzenes may include a temperature of 100 to 300° C., a pressure of 1000 to 7000 kPa-a, a weight hourly space velocity of 1 to 50 hr$^{-1}$ on total feed, and a benzene to polybutylbenzene weight ratio of 1 to 10.

The transalkylation catalyst can comprise one or more of any of the molecular sieves discussed above in relation to the vapor phase alkylation system and can be used with or without a binder or matrix. Generally, however, the transalkylation catalyst is selected from zeolite beta, zeolite Y, Ultrastable Y (USY), Dealuminized Y (Deal Y), mordenite, ZSM-3, ZSM-4, ZSM-5, ZSM-11, ZSM-18, and ZSM-20.

EXAMPLES

Ammonia Uptake Measurement:

A catalyst is loaded in a TGA instrument. The temperature is ramped from about 25° C. to 500° C. under flowing helium on a TGA. The temperature is then and held for 1 hour at 500° C. to remove moisture. The net weight of the dry catalyst is recorded.

After drying, the catalyst is cooled to 250° C. under flowing helium. At 250° C., a 10 wt. % $NH_3$ gas mixture (balanced with helium) is flowed over the catalyst and the weight gain of $NH_3$ adsorption as measured by TGA is monitored. The $NH_3$ uptake by weight is reported as molar equivalent (meq) $NH_3$ per gram of dry catalyst at 250° C.

Example 1

A fresh MCM-22 family catalyst was used and measured by $NH_3$ uptake method of this disclosure. The fresh catalyst has a 0.8591 meq $NH_3$/g catalyst.

Example 2

The fresh catalyst was deactivated by contacting hydrocarbons under aromatic alkylation conditions deactivation. The spent catalyst after deactivation was regenerated in the alkylation reactor with air at about 540° C., about 300 kPa-a pressure, and about 1.25 hr$^{-1}$. The average acidity has dropped from an initial 0.8591 to 0.5750 meq $NH_3$/g catalyst. The air regenerated catalyst has about 33% loss in catalyst acidity as measured by $NH_3$ uptake as compared with the fresh catalyst.

Example 3

The fresh catalyst was deactivated by contacting hydrocarbons under aromatic alkylation conditions. The spent catalyst after deactivation was regenerated outside of the alkylation reactor with air at about 540° C. and about 101.3 kPa-a pressure. The average acidity has dropped from an initial 0.8591 to 0.5550 meq $NH_3$/g catalyst. The ex-situ air regenerated catalyst has also about 33% loss in catalyst acidity as measured by $NH_3$ uptake as compared with the fresh catalyst.

Example 4

The fresh catalyst was deactivated by contacting hydrocarbons under aromatic alkylation conditions. The spent catalyst after deactivation was rejuvenated in the alkylation reactor with nitrogen. The reactor temperature was increased from about 25° C. to at 538° C. at a rate of about 1° C./min. The reactor was then held at 538° C. for about 24 hours. The gas volume hourly velocity for nitrogen was about 0.8 normal cubic meter nitrogen per hour per kilogram of catalyst. The average acidity of the rejuvenated catalyst has dropped from an initial 0.8591 to 0.7216 meq $NH_3$/g catalyst. The rejuvenated catalyst which was rejuvenated under $N_2$ at 538° C. has only resulted in a 15% loss in catalyst acidity as measured by $NH_3$ uptake. This is an improvement of more than 50% as compared with air regeneration. The deactivated catalyst had a carbon content, in the form or coke and/or hydrocarbons, of about 6-10 wt. % based on the total weight of the deactivated catalyst. The rejuvenated catalyst has a carbon content, in the form or coke and/or hydrocarbons, of about 0.09-0.15 wt. % based on the total weight of the deactivated catalyst. The deactivated catalyst had a nitrogen compounds content, as measured by pyro-chemiluminescence (Antek Model 772 Pyroreactor, 720 detector), of about 25-150 wppm based on the total weight of the deactivated catalyst. The rejuvenated catalyst has at least 80% less nitrogen compounds content, as measured by pyro-chemiluminescence (Antek Model 772 Pyroreactor, 720 detector), than the deactivated catalyst.

When numerical lower limits and numerical upper limits are listed herein, ranges from any lower limit to any upper limit are contemplated.

The meanings of terms used herein shall take their ordinary meaning in the art; reference shall be taken, in particular, to Handbook of Petroleum Refining Processes, Third Edition, Robert A. Meyers, Editor, McGraw-Hill (2004). In addition, all patents and patent applications, test procedures (such as ASTM methods), and other documents cited herein are fully incorporated by reference to the extent such disclosure is not inconsistent with this invention and for all jurisdictions in which such incorporation is permitted. Also, when numerical lower limits and numerical upper limits are listed herein, ranges from any lower limit to any upper limit are contemplated. Note further that Trade Names used herein are indicated by a ™ symbol or ® symbol, indicating that the names may be protected by certain trademark rights, e.g., they may be registered trademarks in various jurisdictions.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled in the art to which the invention pertains.

What is claimed is:

1. A method for rejuvenating a catalyst, comprising contacting the catalyst with a gaseous feedstock at rejuvenation conditions for at least one hour to form a rejuvenated catalyst and a gaseous product, wherein said catalyst comprises at least 10 wt. % of a molecular sieve, wherein prior to the contacting step said catalyst comprises from 0.001 wt. % to 45 wt. % of hydrocarbons and 0.001 to 10 wt. % nitrogen containing components, said weight percents based on the total weight of said catalyst prior to the contacting step, wherein said molecular sieve comprises at least one of a MCM-22 family molecular sieve, a molecular sieve having a framework type of *BEA, a molecular sieve having a framework type of FAU, and a molecular sieve having a framework type of MOR, wherein said gaseous feedstock is at least one selected from the group consisting of $N_2$, $H_2$, alkane, He, Ar, CO, nitrogen-containing compounds other than nitrogen, water and $CO_2$, wherein said rejuvenated catalyst comprises at least 50 wt. % less nitrogen containing components than said catalyst prior to the contacting step, wherein said gaseous product has at least a portion of said gaseous feedstock and at least a portion of said hydrocarbons of said catalyst and at least a portion of said nitrogen containing components of said catalyst, wherein said rejuvenation conditions comprise a temperature in the range from about 400 to 600° C., a pressure in the range from about 101.3 kPa-a to 10130 kPa-a, a space hourly velocity in the range of from 0.05 to 10 normal cubic meter gaseous feedstock per hour per kilogram of catalyst.

2. The method of claim 1, wherein said catalyst prior to the contacting step comprises from 0.1 wt. % to 10 wt. % of hydrocarbons and 0.01 to 5 wt. % nitrogen containing components based on the total weight of said catalyst prior to the contacting step.

3. The method of claim 1, wherein said gaseous feedstock comprises less than 5 vol. % of nitrogen containing compounds (not including $N_2$), as impurities.

4. The method of claim 1, wherein said gaseous feedstock comprises less than 1 wt. % water, as an impurity.

5. The method of claim 1, wherein said molecular sieve comprises at least one MCM-22, MCM-49, MCM-56, zeolite beta, zeolite Y, and zeolite mordenite.

6. The method of claim 1, wherein said gaseous feedstock comprises at least 95 wt. % nitrogen.

7. The method of claim 1, wherein said rejuvenation conditions comprise a temperature in the range from about 500 to 560° C., a pressure in the range from about 101.3 kPa-a to 10130 kPa-a, a space hourly velocity in the range of from 0.1 to 2.5 normal cubic meter gaseous feedstock per hour per kilogram of catalyst.

8. The method of claim 1, wherein said rejuvenation conditions comprise a temperature in the range from about 530 to 550° C., a pressure in the range from about 101.3 kPa-a to 10130 kPa-a, a space hourly velocity in the range of from 0.5 to 1.5 normal cubic meter gaseous feedstock per hour per kilogram of catalyst.

9. The method of claim 1, wherein said catalyst is contacted with a gaseous feedstock at rejuvenation conditions for a time period in the range from 1 hour to 10 days.

10. The method of claim 1, further comprising a step of recycling at least a portion of said gaseous product to said contacting step (a).

11. The method of claim 10, recycling less than 90 wt. % of said gaseous product to said contacting step (a).

12. The method of claim 1, further comprising a step of separating at least a portion of said hydrocarbons and at least a portion of said nitrogen containing components in said gaseous product.

13. The method of claim 1, wherein said catalyst is a spent catalyst of an ethylbenzene process or a cumene process.

* * * * *